US011939280B2

(12) United States Patent
Yu et al.

(10) Patent No.: US 11,939,280 B2
(45) Date of Patent: Mar. 26, 2024

(54) METHOD FOR PREPARING ISOPHORONE DIISOCYANATE

(71) Applicant: WANHUA CHEMICAL GROUP CO., LTD., Shandong (CN)

(72) Inventors: Yong Yu, Shandong (CN); Yonghua Shang, Shandong (CN); Lei Zhao, Shandong (CN); Wenbin Li, Shandong (CN); Ye Sun, Shandong (CN); Wei He, Shandong (CN); Xuelei Cui, Shandong (CN); Jingxu Wang, Shandong (CN); Degang Liu, Shandong (CN); Yuan Li, Shandong (CN)

(73) Assignee: WANHUA CHEMICAL GROUP CO., LTD., Shandong (CN)

(*) Notice: Subject to any disclaimer, the term of this patent is extended or adjusted under 35 U.S.C. 154(b) by 347 days.

(21) Appl. No.: 17/295,369

(22) PCT Filed: Dec. 25, 2018

(86) PCT No.: PCT/CN2018/123444
§ 371 (c)(1),
(2) Date: May 19, 2021

(87) PCT Pub. No.: WO2020/124622
PCT Pub. Date: Jun. 25, 2020

(65) Prior Publication Data
US 2022/0002235 A1 Jan. 6, 2022

(30) Foreign Application Priority Data

Dec. 20, 2018 (CN) .......................... 201811567103.0

(51) Int. Cl.
C07D 263/10 (2006.01)
B01J 25/00 (2006.01)
C07C 209/48 (2006.01)
C07C 253/10 (2006.01)
C07C 263/10 (2006.01)

(52) U.S. Cl.
CPC ............. *C07C 263/10* (2013.01); *B01J 25/00* (2013.01); *C07C 209/48* (2013.01); *C07C 253/10* (2013.01); *C07C 2601/16* (2017.05)

(58) Field of Classification Search
CPC .................................................. C07C 263/10
See application file for complete search history.

(56) References Cited

U.S. PATENT DOCUMENTS

| | | |
|---|---|---|
| 3,352,913 A | 11/1967 | Schmitt et al. |
| 5,011,968 A | 4/1991 | Thunberg et al. |
| 5,283,366 A | 2/1994 | Huthmacher et al. |
| 5,364,958 A | 11/1994 | Ishida et al. |
| 2011/0124919 A1 | 5/2011 | Ernst et al. |

FOREIGN PATENT DOCUMENTS

| | | |
|---|---|---|
| CA | 2038126 A1 | 9/1991 |
| CN | 1182108 C | 12/2004 |
| CN | 1675174 A | 9/2005 |
| CN | 101003495 A | 7/2007 |
| CN | 101372464 A | 2/2009 |
| CN | 102531916 A | 7/2012 |
| CN | 102924291 A | 2/2013 |
| CN | 103145586 A | 6/2013 |
| CN | 103228613 A | 7/2013 |
| CN | 103301799 A | 9/2013 |
| CN | 103319372 A | 9/2013 |
| CN | 104761455 A | 7/2015 |
| CN | 105214568 A | 1/2016 |
| CN | 105218422 A | 1/2016 |
| CN | 106554293 A | 4/2017 |
| CN | 107337615 A | 11/2017 |
| CN | 108299240 A | 7/2018 |
| DE | 102010062594 A1 | 6/2012 |
| EP | 0546398 A2 | 6/1993 |
| EP | 0561225 A2 | 9/1993 |
| EP | 0581100 A1 | 2/1994 |
| EP | 3061743 A1 | 8/2016 |
| JP | H04164057 A | 6/1992 |
| JP | H106128214 A | 5/1994 |

(Continued)

OTHER PUBLICATIONS

European Search Report dated Sep. 5, 2022 in the corresponding patent application EP 18943672.8-1110.
Office Action dated May 27, 2022 by the JPO in the corresponding Patent Application No. 2021-520120, with English translation.
Wu, et al.: "A Review of Synthetic Methods of 3-Isocyanatomethyl-3,5,5--trimethylcyclohexyl Isocyanate", Guangzhou Chem. Ind., 41(12), (2013), pp. 1-3 [with English abstract].
Office Action issued in corresponding Chinese Patent Application No. 201811567103.0 dated Nov. 25, 2019, with English translation.
Office Action issued in corresponding Chinese Patent Application No. 201811567103.0 dated Feb. 21, 2020, with English translation.
He., et al.: "Isophorone Diisocyanate and Its Applications", China Academic J. Electronic Publ. House, http://www.cnki.net, (2019), pp. 1-9.

(Continued)

Primary Examiner — Shawquia Jackson
(74) Attorney, Agent, or Firm — Norton Rose Fulbright US LLP; James R. Crawford

(57) ABSTRACT

A method for preparing isophorone diisocyanate by (1) reacting isophorone with hydrogen cyanide in the presence of a catalyst to obtain isophorone nitrile; (2) reacting the isophorone nitrile obtained in step (1) with ammonia gas and hydrogen in the presence of a catalyst to obtain isophorone diamine; and (3) subjecting the isophorone diamine to a phosgenation reaction to obtain the isophorone diisocyanate, wherein the content of impurities containing a secondary amine group in the isophorone diamine that undergoes the phosgenation reaction in step (3) is ≤0.5 wt. The method reduces the content of hydrolyzed chlorine in the isophorone diisocyanate product, improves the yellowing resistance of the product, and the harm due to presence of hydrolyzed chlorine in the product is reduced.

20 Claims, No Drawings

(56) References Cited

FOREIGN PATENT DOCUMENTS

JP        H09169706 A     6/1997
JP        2012532160 A    12/2012

OTHER PUBLICATIONS

Wang, et al.: "Optimized Synthesis of Isophorone Diisocyanate", Guangchou Chem. Ind., 42(13), (2014), pp. 1-4.
International Search Report issued in PCT/CN2018/123444 dated Sep. 26, 2019.

METHOD FOR PREPARING ISOPHORONE DIISOCYANATE

CROSS REFERENCE TO RELATED APPLICATIONS

This application is a national phase under 35 U.S.C. § 371 of International Application No. PCT/CN2018/123444 filed Dec. 25, 2018, which claims the benefit of priority to Chinese Application No. 201811567103.0 filed on Dec. 20, 2018. The entire contents of these applications are hereby incorporated by reference in their entirety.

TECHNICAL FIELD

The present disclosure relates to a method for preparing an aliphatic isocyanate, and specifically, to a method for preparing isophorone diisocyanate.

BACKGROUND

Isophorone diisocyanate (IPDI), which is a colorless or light yellow liquid at room temperature, is an aliphatic isocyanate and also is an alicyclic isocyanate. The reaction activity of IPDI is lower than that of aromatic isocyanate, its vapor pressure is low, and its toxicity is smaller than that of isocyanate. Due to the absence of benzene ring in its structure, IPDI has excellent weather resistance and thus can be used to prepare high-grade polyurethane materials having photostability, weather resistance and excellent mechanical properties, such as elastomers, waterborne polyurethane dispersions, ultraviolet (UV) resin and the like. IPDI can also be self-polymerized to form a polyfunctional polyisocyanate, and the surface of the coating prepared by the polyfunctional polyisocyanate can be dried quickly so the polyfunctional polyisocyanate has an excellent application in automobile refinishing paint. The above application has strict requirements for the hydrolyzed chlorine content and color number of the IPDI monomer.

There are many reasons for the high hydrolytic chlorine content and high color of the IPDI monomer, so different methods are needed to avoid these problems. U.S. Pat. No. 5,364,958 introduces a method for preparing isocyanate, in which phosgene is removed from the reaction solution and a heat treatment is performed on this reaction solution in the presence of hot HCl gas to reduce the color number of the product. EP0581100 also proposes a method for preparing light-colored isocyanate, in which a chemical reducing agent is added after phosgenation and before solvent removal to obtain a light-colored product. CN00809301.6 provides a method for implementing the preparation of light-colored isocyanates by controlling the contents of bromide and iodide in phosgene. EP0561225 also describes a process for the preparation of light-colored isocyanates, in which the isocyanates obtained after phosgenation of the corresponding amines are hydrogenated at a pressure of from 1 to 150 bar and a temperature of from 100 to 180° C. to give light-colored isocyanate products. EP0546398 and EP0446781 implement the purpose of the reduction of the color number of isocyanate prepared after the phosgenation reaction by pre-treating raw amine. The former provides a process in which the amine is acidified prior to phosgenation, and the latter provides a method in which the amine is pretreated with hydrogen before phosgenation and the amine after acidification or hydrogen pretreatment is reacted with phosgene to yield a light-colored isocyanate.

SUMMARY

In view of the above, the present disclosure provides a method for preparing isophorone diisocyanate. This method can effectively reduce the content of hydrolyzed chlorine in the isophorone diisocyanate product, effectively improve the yellowing resistance of the product, and also reduce the harm of causing an unqualified downstream article due to the presence of hydrolyzed chlorine in the product.

To achieve the objects of the present disclosure, the present disclosure adopts the following technical solution:

(1) reacting isophorone with hydrogen cyanide in the presence of a catalyst to obtain isophorone nitrile;

(2) reacting the isophorone nitrile obtained in step (1) with ammonia gas and hydrogen in the presence of a catalyst to obtain isophorone diamine; and (3) subjecting the isophorone diamine to a phosgenation reaction to obtain isophorone diisocyanate, wherein the content of impurities containing a secondary amine group in the isophorone diamine that is subjected to the phosgenation reaction in step (3) is less than or equal to 0.5 wt %, preferably less than or equal to 0.3 wt %, and further preferably less than or equal to 0.1 wt %.

Through the method of the present disclosure, the content of impurities containing a secondary amine group in the isophorone diamine is controlled to be less than or equal to 0.5 wt % and the isophorone diamine (IPDA) having a low secondary amine impurity content is subjected to phosgenation to give an isophorone diisocyanate product in which the content of hydrolyzed chlorine is 0.005% or less, thereby improving the yellowing resistance of the product and meanwhile reducing the reject ratio of downstream articles from the source.

In each step of the present disclosure, small molecules such as solvents and monomers in each step can be removed by technical means known in the art, and in some specific embodiments, purification may be performed by means of rectification, distillation, crystallization, or the like.

For the preparation of isocyanate, it is inevitable that there will be a small amount of hydrolyzed chlorine in the final product obtained. In one aspect, the residual hydrolyzed chlorine causes the yellowing of the isocyanate monomer. In another aspect, the presence of the hydrolyzed chlorine makes the reaction fluctuate violently in the downstream application process and even leads to an unqualified downstream product. Therefore, it is necessary to control the content of hydrolyzed chlorine in the isocyanate product.

The reaction principle of preparing isocyanate by reacting primary amine with phosgene is as follows:

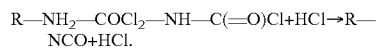

From the reaction process, the amine and phosgene first form carbamoyl chloride, and then one molecular hydrogen chloride is removed to obtain the corresponding isocyanate. In this process, the phosgene provides a carbonyl group, and all hydrolyzed chlorine is combined with hydrogen on the primary amine to form hydrolyzed hydrogen chloride and then discharged. Therefore, theoretically, no hydrolyzed chlorine remains.

However, if secondary amine impurities are present in the raw amine, the reaction as shown in the following formula I occurs during the phosgenation reaction:

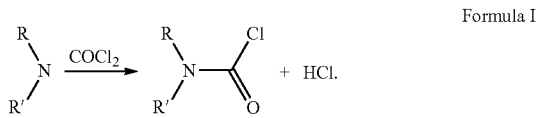

Formula I

From the above reaction process, the impurities containing a secondary amine group first forms carbamoyl chloride with phosgene. However, since there is no hydrogen on the nitrogen of the formed carbamoyl chloride, it is impossible to further remove hydrogen chloride to obtain isocyanate. The increase of the content of carbamoyl chloride will cause the increase of the content of hydrolyzed chlorine in the isocyanate product, thereby affecting the yellowing resistance of the product.

The inventors have found that there are three main sources of isophorone secondary amine.

One source is that the secondary amine is obtained by removing one molecular ammonia gas from the amine group of the molecule of isophorone diamine, in which the specific reaction process is as follows:

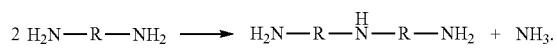

Due to its large molecular weight, the secondary amine obtained in this process may relatively easily separate from the isocyanate monomer product even if carbamoyl chloride is formed in the phosgenation reaction stage, and finally cannot remain in the isocyanate monomer product.

A second source is the preparation of isophorone diamine, that is, the isophorone secondary amine is formed in the process of the preparation of isophorone diamine (IPDA) by performing the amination hydrogenation reaction of isophorone nitrile, ammonia gas and hydrogen in step (2) of the present disclosure.

The inventors have found that the ammonia gas used in this process may contain a small amount of methylamine impurities. The technology of the synthesis of ammonia from nitrogen and hydrogen is known in the industry, in which nitrogen generally comes from air separation and its purity can reach a relatively high level. However, the hydrogen preparation process is relatively diversified. Considering the factors of energy consumption, material consumption and industrial park integration, hydrogen is usually prepared by alkane cracking, steam reforming, or even refining of hydrogen-containing tail gas from the refinery. The hydrogen obtained by such a method more or less contains a small amount of impurities which react and form methylamine in the process of ammonia synthesis.

If methylamine is present in the ammonia gas used in step (2) of the present disclosure, the reaction as shown in the following formula II occurs:

Formula II

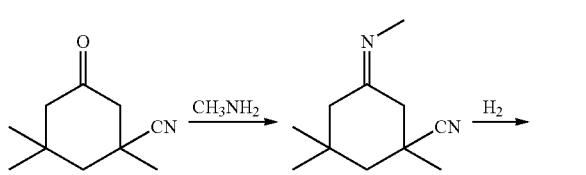

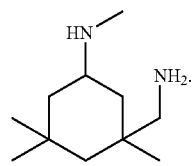

The impurities containing the secondary amine group obtained in formula II continuously cause the reaction of formula I to form carbamoyl chloride, thereby causing the deterioration of yellowing resistance of the product. Since the molecular weight of the impurities containing the secondary amine group obtained in this process is close to the molecular weight of isophorone diamine (IPDA), the separation of the impurities containing the secondary amine group from isophorone diamine (IPDA) is costly. Meanwhile, the cost of the separation of carbamoyl chloride obtained after the phosgenation of the secondary amine in the process of formula II from corresponding isocyanate is relatively high.

Therefore, to reduce the content of secondary amine obtained in the process of formula II and further reduce the content of hydrolyzed chlorine in carbamoyl chloride in the final isocyanate, the content of methylamine in ammonia gas used in the synthesis and preparation of isophorone diamine (IPDA) needs to be controlled. In a preferred embodiment of the present disclosure, the content of methylamine in the ammonia gas in step (2) is controlled to be less than or equal to 0.5 wt %, preferably less than or equal to 0.3 wt %, and further preferably less than or equal to 0.1 wt %, for example, 0.02 wt % and 0.05 wt %.

A third source is that the isophorone secondary amine is formed in the process of obtaining isophorone nitrile (IPN) by reacting isophorone with hydrogen cyanide (HCN) in step (1) of the present disclosure since HCN in the production process more or less contains a small amount of olefins.

The inventors have found that the industrial production methods of HCN used in this process mainly include Andrussow process, BMA process, acrylonitrile byproduct process, light oil cracking process and the like, but based on the mainstream processes of producing HCN, HCN obtained by such processes will more or less contain a small amount of olefins.

In step (1) of the present disclosure, the presence of olefins in hydrogen cyanide results in the occurrence of the reaction as shown in the following formula III:

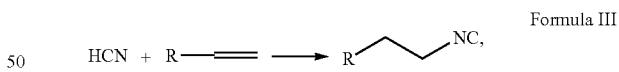

Formula III wherein R is H or $C_xH_y$, wherein x is 1 to 2, and y is 3 or 5.

The isonitrile-based impurities obtained in formula III react with isophorone (IP) under the conditions described in step (1) of the present disclosure, and the reaction is shown in the following formula IV:

Formula IV

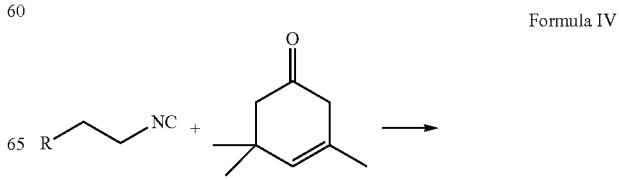

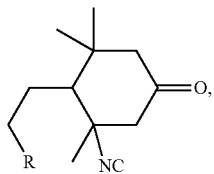

wherein R is H or $C_xH_y$, wherein x is 1 to 2, and y is 3 or 5.

The isonitrile-based impurities obtained in formula IV are continuously subjected to the ammonification hydrogenation reaction in step (2) to obtain the impurities containing the secondary amine group as follows:

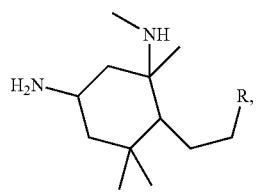

wherein R is H or $C_xH_y$, wherein x is 1 to 2, and y is 3 or 5.

When R in the impurities containing the secondary amine group is H or x is less than or equal to 2, it is difficult to separate the impurities containing the secondary amine group from isophorone diamine (IPDA), and it is also difficult to separate the chlorine-containing impurities obtained after phosgenation from isophorone diisocyanate (IPDI).

Therefore, to reduce the content of the secondary amine obtained from the isonitrile-based impurities and further reduce the content of hydrolyzed chlorine in the final isocyanate, the content of the olefins in the HCN used in the synthesis and preparation of isophorone nitrile (IPN) needs to be controlled. In a preferred embodiment of the present disclosure, the content of olefins in the hydrogen cyanide in step (1) is less than or equal to 0.3 wt %, preferably less than or equal to 0.1 wt %, for example, 0.01 wt % and 0.05 wt %. Specifically, the olefins include one or more of ethylene, propylene, butylene, butadiene or isobutylene.

In step (1) of the present disclosure, the reaction process of isophorone with hydrogen cyanide in the presence of a catalyst can be found in Chinese patent No. CN103301799B which is incorporated herein by reference. Specifically, the hydrogen cyanide, isophorone, and catalyst are continuously fed to a reactor at a total flow rate of 1 to 10 ml/min according to a set material ratio (for the specific structure of the reactor, reference may be made to Patent Document CN103301799B). Under the conditions of a set reaction temperature, pressure, and residence time, the reaction liquid is continuously produced to obtain an isophorone nitrile crude product, and then the isophorone nitrile pure product is obtained by separation. In some specific embodiments, the temperature of the reaction in step (1) is 50° C. to 200° C., further preferably 80° C. to 160° C., for example, 100° C. and 120° C., the reaction pressure is 0 to 1.5 Mpa absolute, for example, 0.5 Mpa absolute and 1 Mpa absolute, and the residence time of the reaction material is 1 to 60 min, further preferably 1 to 40 min, for example, 5 min and 30 min.

In the preparation process of the present disclosure, in step (1), the material molar ratio of hydrogen cyanide, isophorone and catalyst is 1:1-3:0.005-0.03, and further preferably, the above ratio is 1:1-1.5:0.006-0.015, for example, 1:1.2:0.01. In some specific embodiments, the catalyst in step (1) is an oxide, a hydroxide, a cyanide, or an alkyl alcoholate of an alkali metal or alkaline earth metal, a carbonate of an alkali metal or alkaline earth metal, a tertiary amine, a quaternary phosphine base, or a quaternary ammonium base, further preferably one or more of sodium hydroxide, sodium cyanide, lithium hydroxide, calcium hydroxide, sodium methoxide, sodium ethoxide, triethylamine, tetramethylammonium hydroxide, tetramethylammonium chloride, or tetramethylammonium bromide.

In step (2) of the present disclosure, the method of the production of isophorone diamine by isophorone nitrile catalyzed by ammonia hydrogenation can be found in Chinese patent No. CN102924291B which is incorporated herein by reference. Specifically, the above method includes the following steps: a) reacting 3-cyano-3,5,5-trimethylcyclohexanone (that is, isophorone nitrile) with $NH_3$ to obtain a product containing 3-cyano-3,5,5-trimethylcyclohexylimine; b) mixing the product obtained in step a) with a basic compound in the presence of hydrogen, $NH_3$ and a first hydrogenation catalyst whose space velocity is 0.5 to 10 g of 3-cyano-3,5,5-trimethylcyclohexanone/(milliliter of catalyst·hour) to obtain a product containing 3-aminomethyl-3,5,5-trimethylcyclohexylamine and 3-cyano-3,5,5-trimethylcyclohexylamine; and c) mixing the product obtained in step b) with an acidic compound, and converting 3-cyano-3,5,5-trimethylcyclohexylamine in the product obtained in step b) to 3-aminomethyl-3,5,5-trimethylcyclohexylamine in the presence of hydrogen, $NH_3$ and a second hydrogenation catalyst; wherein the content of 3-cyano-3,5,5-trimethylcyclohexylamine in the product obtained in step b) is 5 to 20 wt %, and the acidic compound in step c) is an organic acid.

In the preparation process of step (2) of the present disclosure, the reaction temperature of step 2) is 20° C. to 100° C., further preferably 20° C. to 70° C., for example, 40° C. and 60° C., and the pressure is 0.5 to 30 MPa, further preferably 1 to 20 MPa, for example, 10 MPa and 15 MPa.

In the preparation process of the step (2) of the present disclosure, a catalyst may or may not be used in step a). If a catalyst is used, the catalyst may be an acidic metal oxide, an inorganic ion exchange resin or an organic ion exchange resin, such as alumina, titanium dioxide, zirconium dioxide, silica, zeolite, and the like.

The preparation process of step a) may be carried out under a hydrogen atmosphere or in the absence of hydrogen, preferably under a hydrogen atmosphere. The molar ratio of hydrogen to isophorone nitrile (IPN) is 3:1 to 1000:1, preferably 4:1 to 500:1, more preferably 10:1 to 500:1, further preferably 15:1 to 300:1, and particularly preferably 20:1 to 100:1.

The preparation process of step a) is preferably carried out without adding any solvent, or may be carried out in the presence of an alcohol or an ether solvent, such as ethanol, butanol or tetrahydrofuran.

The preparation of step a) is preferably carried out continuously, generally in a pressure vessel, preferably using a tubular reactor in which a catalyst for the formation of the imine reaction is present in the form of a fixed bed. In this reaction, the conversion of 3-cyano-3,5,5-trimethylcyclohexanone (IPN) to 3-cyano-3,5,5-trimethylcyclohexylimine (IPNI) is usually 80% or more, even 90% or more, and the maximum conversion can be 95% or more.

In the preparation of step (2) of the present disclosure, the reaction temperature of step b) is 50° C. to 130° C., more preferably 60° C. to 100° C., for example, 70° C. and 80° C., and the pressure is 10 to 30 MPa, and further preferably 15 to 20 MPa, for example, 17 MPa and 19 MPa.

The basic compound in step b) is a basic metal compound including an oxide, a hydroxide or a carbonate of an alkali metal, an oxide, a hydroxide or a carbonate of an alkaline earth metal, or an oxide, a hydroxide or a carbonate of a rare earth metal, preferably an oxide, a hydroxide or a carbonate of an alkali metal, or an oxide, a hydroxide or a carbonate of an alkaline earth metal, and more preferably LiOH, NaOH or KOH. The basic compound is used in the form of a solution, and the solvent may be water, an alcohol or an ether, preferably an alcohol solution of the basic compound, and more preferably a methanol or an ethanol solution of the basic compound, and the concentration of the solution is 0.1 to 10 wt %, preferably 1 to 5 wt %, for example, 2 wt % and 4 wt %. The mass ratio of the basic compound in step b) to 3-cyano-3,5,5-trimethylcyclohexanone (IP) in step a) is 1:100-1000, further preferably 1:200-750, for example, 1:500 and 1:250.

Step b) is carried out at a temperature of 50° C. to 130° C. and an absolute pressure of 10 to 30 MPa, preferably at a temperature of 60° C. to 100° C. and an absolute pressure of 15 to 20 MPa. The molar ratio of $NH_3$ to isophorone nitrile (IPN) is 5:1-200:1, preferably 10:1-100:1, and more preferably 20:1-80:1, for example, 50:1. The molar ratio of hydrogen to IPN is 3:1-1000:1, preferably 4:1-500:1, more preferably 10:1-500:1, further preferably 15:1-300:1, and particularly preferably 20:1-100:1. Hydrogen may be mixed with the IPNI material after the imidization reaction and before the hydrogenation reaction, or may also be mixed with IPN and $NH_3$ at the beginning.

In the preparation process of step (2) of the present disclosure, the first hydrogenation catalyst in step b) is the same as or different from the second hydrogenation catalyst in step c), and the active component is a cobalt or nickel hydrogenation catalyst, for example, a supported cobalt/nickel catalyst or a skeletal cobalt/nickel catalyst, preferably a supported/skeletal cobalt catalyst, and more preferably Raney cobalt.

The hydrogenation reaction in step c) of the present disclosure is carried out continuously in a pressure vessel, for example in a hydrogenation reactor, preferably in a tubular reactor, and more preferably in a trickle bed reactor. The hydrogenation reactor may be a constant temperature reactor or a variable temperature reactor, for example, an adiabatic reactor.

In some specific embodiments, the acidic compound in step c) is an organic acid. The organic acid may be an organic monoacid of $C_1$-$C_{40}$, an organic diacid of $C_1$-$C_{40}$, or an organic polyacid of $C_1$-$C_{40}$, preferably an organic monoacid of $C_1$-$C_{16}$, an organic diacid of $C_1$-$C_{16}$, or an organic polyacid of $C_1$-$C_{16}$, and more preferably formic acid or acetic acid. The mass ratio of the acidic compound to IPN obtained in step b) is 1:100-1:1000. The acidic compound may be used in the form of a solution, and the solvent may be water, an alcohol or an ether, preferably an alcohol solution of the acidic compound, and more preferably a methanol solution or an ethanol solution of the acidic compound, and the solution concentration is 0.1 to 10 wt %, preferably 1 to 5 wt %.

Step c) is carried out at a temperature of 50° C. to 130° C. and an absolute pressure of 10 to 30 MPa, preferably at a temperature of 100° C. to 130° C. and an absolute pressure of 15 to 20 MPa. The molar ratio of hydrogen to IPN obtained in step b) is 3:1-1000:1, preferably 4:1-500:1, more preferably 10:1-500:1, further preferably 15:1-300:1, and particularly preferably 20:1-100:1.

In some embodiments of the present disclosure, the phosgenation reaction in step (3) may be any one of a gas phase phosgenation reaction, a cold-hot phosgenation reaction, and a salification phosgenation reaction, wherein the phosgene reaction is a reaction of isophorone diamine with one or more of phosgene, diphosgene, triphosgene, fluorophosgene or bromophosgene.

The phosgenation reaction may be carried out in gas phase, and for the specific method, reference is made to Chinese patent No. CN105214568A which is incorporated herein by reference. Specifically, the method includes: a) vaporizing amine to an amine gas stream containing amine droplets; b) removing the amine droplets contained in the amine gas stream to obtain an amine gas stream substantially free of amine droplets; and c) subjecting the amine gas stream substantially free of amine droplets to a gas phase phosgenation reaction with phosgene to obtain an isocyanate, and meanwhile removing the amine droplets contained in the amine gas stream using a heater. For the specific structure of the heater, reference is made to Patent Document CN105214568A.

The temperature of the above reaction is 200° C. to 550° C., preferably 250° C. to 400° C., for example, 300° C. and 320° C., and the reaction pressure is 0.01 to 1 MPa, preferably 0.03 to 0.3 MPa, for example, 0.08 MPa and 0.2 MPa. In some specific embodiments, the mixed gas after the reaction of phosgene and isophorone diamine (IPDA) needs to be absorbed and cooled using a liquid inert medium or/and a mixture of inert medium and isocyanate. The inert gas is preferably nitrogen, argon, or a steam of toluene, xylene, chlorobenzene, or o-dichlorobenzene, and the liquid inert medium is selected from all inert liquids suitable for the preparation of isocyanates, preferably chlorobenzene, dichlorobenzene, o-dichlorobenzene, toluene, chlorotoluene, xylene and/or mixtures thereof.

The phosgenation reaction may be carried out in liquid phase, and for the specific method, reference is made to Chinese Patent No. CN103319372B, which is incorporated herein by reference. Specifically, the method includes: a) performing a cold reaction at a temperature of 0 to 130° C., preferably 40° C. to 70° C. and an absolute pressure of 0.1 to 1 MPa using toluene, chlorobenzene, benzene, dichlorobenzene, cyclohexane, xylene or mixtures thereof as the solvent, particularly preferably chlorobenzene or dichlorobenzene as the solvent, and reacting with a superstoichiometric amount of phosgene with a residence time of 2 to 120 min, preferably 5 to 45 min; and b) performing a hot reaction at a temperature of 60° C. to 190° C., preferably 110° C. to 165° C. and an absolute pressure of 0.1 to 1 MPa using toluene, chlorobenzene, benzene, dichlorobenzene, cyclohexane, xylene or mixtures thereof as the solvent, particularly preferably chlorobenzene or dichlorobenzene as the solvent, and reacting with a superstoichiometric amount of phosgene with a reaction residence time of 0.5 to 5 h, preferably 1 to 4 h.

The phosgenation reaction may be a salification phosgenation reaction carried out in hydrogen chloride and/or carbon dioxide, and for the specific method, reference is made to Chinese patent Nos. CN105218422B and CN107337615A which are incorporated herein by reference. Specifically, the method includes: a) reacting hydrogen chloride or/and carbon dioxide with an amine in an inert solvent for salification reaction, wherein the molar equivalent ratio of hydrogen chloride to the amino group of the amine is 1-2.5:1, preferably 1.2-2:1, the molar equivalent ratio of carbon dioxide to the amino group of the amine is 0.5-5:1, preferably 0.6-3:1, the mass ratio of the solvent to the amine is 25-5:1, preferably 20-5:1, the temperature of the salification reaction is 0-50° C., preferably 5° C.-30° C., the pressure is an absolute pressure of 0.1 to 1 MPa, preferably 0.2 to 0.5 MPa, the reaction residence time is 1 to 15 min, preferably 5 to 10 min, and the reaction pressure is an absolute pressure of 0.1 to 1 MPa, preferably 0.2 to 0.5 MPa; and the reaction solution of hydrochloride or carbonate obtained after the salification reaction in step a) entering into step b) for phosgenation reaction at a temperature of 100° C. to 170° C., preferably 110° C. to 165° C. and an absolute pressure of 0.1 to 1 MPa, preferably 0.2 to 0.5 MPa, and reacting with a superstoichiometric amount of phosgene with the reaction residence time of 1 to 5 h, preferably 1.5 to 4 h, wherein the inert solvent is toluene, chlorobenzene, benzene, dichlorobenzene, cyclohexane, xylene or mixtures thereof, more preferably chlorobenzene or dichlorobenzene.

In some specific embodiments, the phosgene in the phosgenation reaction is excessive, and the excess phosgene after the phosgenation reaction is preferably removed at about 50° C. to 180° C. and an absolute pressure of 0.05 to 0.1 MPa.

Compared with the existing art, the present disclosure has the following advantages.

The method of the present disclosure effectively controls the generation of secondary amine impurities in the preparation process of isophorone diamine (IPDA) and performs phosgenation through isophorone diamine (IPDA) having a low secondary amine impurity content to give the isophorone diisocyanate product in which the content of hydrolyzed chlorine is 0.005%, thereby improving the yellowing resistance of the product and meanwhile reducing the reject ratio of downstream articles from the source.

DETAILED DESCRIPTION

The technical solutions and effects thereof of the present disclosure will be further described hereinafter through the specific examples. It is to be understood that the examples described below are intended to illustrate the present disclosure but are not be construed to limit the scope thereof. The simple modifications made to the present disclosure in according with the concept of the present disclosure are within the scope of the present disclosure.

The test methods used in the embodiments of the present disclosure are as follows:

(1) The quantitative analysis of methylamine in ammonia gas was carried out on gas chromatography under the following conditions:

chromatographic column was PLOT GDX-203 (specification: 30 m*0.53 mm*5.00 μm), the injector temperature was 50° C., the column flow was 1.5 ml/min, the column temperature was 50° C. and maintained for 1 min and then raised to 135° C. at 5° C./min and maintained for 8 min, the detector temperature was 140° C., the $H_2$ flow was 60 ml/min, and the air flow was 350 ml/min.

(2) The quantitative analysis of the impurities containing the secondary amine group in IPDA was carried out on gas chromatography under the following conditions:

chromatographic column was Agilent HP-5 (specification: 30 m*0.32 mm*0.25 μm), the injector temperature was 280° C., the split ratio was 30:1, the column flow was 1.5 ml/min, the column temperature was 100° C. and maintained for 0.5 min and then raised to 260° C. at 15° C./min and maintained for 8 min, the detector temperature was 280° C., and the $H_2$ flow was 35 ml/min.

(3) The analysis of the content of hydrolyzed chlorine in IPDI used the method mentioned in the Chinese national standard GB/T 12009.2-1989.

(4) The analysis of the chromaticity index in IPDI used the method mentioned in the Chinese national standard GB/T605-2006.

(5) The quantitative analysis of the content of olefins in hydrogen cyanide was carried out on the gas chromatography under the following conditions:

chromatographic column was Agilent HP-5 (specification: 30 m*0.53 mm*5.00 μm), the injector temperature was 50° C., the column flow was 1.5 ml/min, the column temperature was 50° C. and maintained for 1 min and then raised to 135° C. at 5° C./min and maintained for 8 min, the detector temperature was 140° C., the $H_2$ flow was 60 ml/min, and the air flow was 350 ml/min.

Example 1

(1) Isophorone was supplied to a preheater at a rate of 200 kg/h and preheated to the reaction temperature of 120° C., and then isophorone, HCN and sodium methoxide serving as the basic catalyst in a molar ratio of 2:1:0.003 were supplied to the reactor disclosed in Example 1 of CN103301799B which operated under the operating conditions as disclosed in CN103301799B and reacted at an absolute pressure of 1 MPa to obtain isophorone nitrile (IPN) after 25 min of reaction.

The content of olefinic impurities in the HCN used in step (1) was 0.01 wt %.

(2) The isophorone nitrile obtained in step (1) was reacted with ammonia gas and hydrogen in the presence of a catalyst, wherein the specific reaction was as follows:

a) The isophorone nitrile obtained in step (1) was reacted with ammonia gas in a tubular reactor at a temperature of 60° C. and an absolute pressure of 15 MPa to obtain 3-cyano-3,5,5-trimethylcyclohexylimine, wherein the molar ratio of ammonia gas to isophorone nitrile was 50:1.

b) In the presence of a hydrogenation catalyst Raney cobalt at a space velocity of 1.5 g of 3-cyano-3,5,5-trimethylcyclohexanone/(milliliter of catalyst·hour), hydrogen, $NH_3$, and 3-cyano-3,5,5-trimethylcyclohexylimine obtained in step a) were mixed in 3% KOH ethanol solution and then reacted at a temperature of 80° C. and an absolute pressure of 18 MPa to obtain a product containing 3-aminomethyl-3,5,5-trimethylcyclohexylamine (IPDA) and 3-cyano-3,5,5-trimethylcyclohexylamine.

In step b), the mass ratio of the KOH ethanol solution to the added isophorone nitrile was 1:600, the molar ratio of $NH_3$ to isophorone nitrile was 50:1, and the molar ratio of hydrogen to isophorone nitrile was 80:1.

c) In the presence of a hydrogenation catalyst Raney cobalt at a space velocity of 1.8 g of 3-cyano-3,5,5-trimethylcyclohexanone/(milliliter of catalyst·hour), hydrogen, $NH_3$, and the product containing 3-aminomethyl-3,5,5-trimethylcyclohexylamine (IPDA) and 3-cyano-3,5,5-trimethylcyclohexylamine obtained in step b) were mixed in 3% acetic acid-ethanol solution and then reacted at a temperature of 120° C. and an absolute pressure of 18 MPa to convert 3-cyano-3,5,5-trimethylcyclohexylamine to 3-aminomethyl-3,5,5-trimethylcyclohexylamine (IPDA). After the test, the content of impurities containing the secondary amine group in IPDA was 0.4 wt %.

In step c), the mass ratio of the acetic acid-ethanol solution to IPN obtained in step (1) was 1:500, the molar ratio of hydrogen to IPN obtained in step (1) was 30:1, and the molar ratio of ammonia gas to IPN obtained in step (1) was 50:1.

The content of methylamine in the ammonia gas used in each step of step (2) was 0.45 wt %.

(3) The obtained IPDA was gasified and heated to 355° C. by using the heater mentioned in Example 1 of Chinese Patent No. CN105214568A, and under the protection of nitrogen gas, the gasified IPDA and gaseous phosgene heated to 355° C. were continuously fed into the reactor through respective feed pipes and then reacted at an absolute pressure of 0.05 MPa and a temperature of 360° C., wherein the feed amount of IPDA was 800 Kg/h and the feed amount of the phosgene was 3000 Kg/h. The mixed gas obtained after the reaction was rapidly cooled to 100° C. by means of a gas injection absorption device using o-dichlorobenzene solution to obtain a photochemical liquid containing the product IPDI. Excess phosgene was removed at 180° C. and an absolute pressure of 0.1 MPa to obtain a crude IPDI product free of phosgene. The crude product was subsequently rectified by means of a rectifying column, and a IPDI product under the distillation of 0.5 KPa and 150° C. to 160° C. was collected, whose yield and purity were 95% and 99.5%, respectively.

Example 2

This example differs from Example 1 in that step (3) was carried out in a reaction kettle mentioned in Chinese patent No. CN103319372B:

a) cold reaction: the IPDA obtained in step (2) was prepared as a solution in which the content of IPDA was 15% by mass using chlorobenzene as the solvent and preheated to 40° C., and the IPDA solution was fed to a reaction kettle containing chlorobenzene simultaneously with a liquid phosgene at −5° C. to perform a liquid phosgenation reaction, wherein the feed amount of IPDA was 400 Kg/h, the feed amount of phosgene of the cold reaction was 1500 kg/h, the temperature of the cold reaction was controlled at 60° C., and the residence time was 5 min.

b) hot reaction: a photochemical liquid containing the product IPDI was obtained in the conditions that the temperature was controlled at 140° C. and the residence time was 2 h; excess phosgene was removed at 180° C. and an absolute pressure of 0.1 MPa to obtain a crude product IPDI free of phosgene; and the crude product was subsequently rectified by means of a rectifying column, and an IPDI product under the distillation of 0.5 KPa and 150° C. to 160° C. was collected, whose yield and purity were 96% and 99.5%, respectively.

Example 3

This example differs from Example 1 in the following aspects:

1. The content of olefins in hydrogen cyanide in step (1) was 0.25 wt %.
2. The content of impurities containing the secondary amine group in IPDA obtained after step (2) was 0.45 wt %.
3. In step (3), the preparation was carried out in a reaction kettle mentioned in Example 1 of Chinese patent No. CN105218422B using the following method:

a) 1000 Kg of o-dichlorobenzene was pre-added in a salification reaction kettle as the reaction solvent, a circulation pump was turned on and stirred the reaction solution, hydrogen chloride compressed gas was supplied through a pre-mixer into the reactor at a speed of 50 mol/min and stirred for 15 min, and a mixture liquid of IPDA and o-dichlorobenzene (the concentration of fed amine was 20 wt %) was heated through a raw material preheater to 30° C. and fully contacted with hydrogen chloride gas at a flow rate of 335 Kg/h to perform a salification reaction. The reaction was cooled with external circulating cooling water to remove a part of the heat of the reaction, wherein the flow rate of the circulating liquid was about 5 m³/h and the temperature of the reaction liquid was maintained at 30° C. to 45° C. After 3 hours of feeding, the mixed liquid of IPDA and o-dichlorobenzene was stopped, and the HCl gas was continuously introduced for 30 min.

b) The resulting IPDA hydrochloride slurry was transferred to a photochemical reactor having a phosgene inlet pipe, gas phase condensation reflux and stirring. The photochemical reaction kettle was heated up while stirring was started. After the temperature reached 60° C., phosgene was introduced into the photochemical reaction kettle, wherein the feed rate of phosgene was 50 mol/min and the reaction temperature was 130° C. The phosgene feeding was stopped after the photochemical liquid was clarified to obtain the salification photochemical reaction liquid. Excess phosgene was removed at 180° C. and an absolute pressure of 0.1 MPa to obtain a crude IPDI product free of phosgene. The crude product was subsequently rectified by means of a rectifying column, and an IPDI product under the distillation of 0.5 KPa and 150° C. to 160° C. was collected, whose yield and purity were 95% and 99.5%, respectively.

Example 4

This example differs from Example 3 in that the content of methylamine in the ammonia gas used in each step of step (2) was 0.25 wt % and the content of impurities containing the secondary amine group in the obtained IPDA was 0.35 wt %.

Comparative Example 1

This comparative example differs from Example 1 in that the content of methylamine in the ammonia gas used in each step of step (2) was 0.75 wt %, the content of impurities containing the secondary amine group in the obtained IPDA was 0.75 wt %, and the yield and purity of the product were 95% and 99.5%, respectively.

Comparative Example 2

This comparative example differs from Example 1 in that the content of olefinic impurities in the HCN used in step (1) was 0.75 wt %, the content of methylamine in the ammonia gas used in each step of step (2) was 0.75 wt %, the content of impurities containing the secondary amine group in the obtained IPDA was 0.95 wt %, and the yield and purity of the product were 95% and 99.5%, respectively.

Comparative Example 3

This comparative example differs from Example 3 in that the content of methylamine in the ammonia gas used in each step of step (2) was 0.75 wt %, the content of impurities containing the secondary amine group in the obtained IPDA was 0.75 wt %, and the yield and purity of the product were 96% and 99.5%, respectively.

Comparative Example 4

This comparative example differs from Example 1 in that the content of methylamine in the ammonia gas used in each step of step (2) was 0.75 wt %, the content of impurities containing the secondary amine group in the obtained IPDA was 0.75 wt %, and the yield and purity of the product were 95% and 99.5%, respectively.

Comparative Example 5

This comparative example differs from Example 1 in that the content of olefinic impurities in the HCN used in step (1) was 0.75 wt %, the content of impurities containing the secondary amine group in the IPDA obtained in step (2) was 0.85 wt %, and the yield and purity of the product were 95% and 99.5%, respectively.

After testing, parameters in the above examples and comparative examples and the test results of the content and chromaticity of hydrolyzed chlorine in the products are shown in Table 1.

TABLE 1

| | Step (1) Content of olefins in hydrogen cyanide (wt %) | Step (2) | | Step (3) | |
|---|---|---|---|---|---|
| | | Content of methylamine in ammonia gas (wt %) | Content of impurities containing the secondary amine group in IPDA (wt %) | Hydrolyzed chlorine (ppm) | Chromaticity (Hazen) |
| Example 1 | 0.01 | 0.45 | 0.4 | 12 | 10 |
| Example 2 | 0.01 | 0.45 | 0.4 | 8 | 5 |
| Example 3 | 0.25 | 0.45 | 0.45 | 10 | 7.5 |
| Example 4 | 0.25 | 0.25 | 0.35 | 15 | 10 |
| Comparative example 1 | 0.01 | 0.75 | 0.75 | 80 | 75 |
| Comparative example 2 | 0.75 | 0.75 | 0.95 | 95 | 85 |
| Comparative example 3 | 0.25 | 0.75 | 0.75 | 89 | 60 |
| Comparative example 4 | 0.01 | 0.75 | 0.75 | 87 | 55 |
| Comparative example 5 | 0.75 | 0.45 | 0.85 | 90 | 70 |

As can be seen from the data in the above table, in the present disclosure, the content of olefins in the raw material HCN and the content of methylamine in the ammonia gas in the preparation process of the IPDA are controlled so that the secondary amine impurities in the IPDA are controlled 0.5 wt % or less and thus the chromaticity of the IPDI obtained after phosgenation and the hydrolyzed chlorine in the IPDI are at a very low level, thereby reducing the reject ratio of the downstream product from the source.

What is claimed is:

1. A method for preparing isophorone diisocyanate, comprising the following steps:
   (1) reacting isophorone with hydrogen cyanide in the presence of a catalyst to obtain isophorone nitrile;
   (2) reacting the isophorone nitrile obtained in step (1) with ammonia gas and hydrogen in the presence of a catalyst to obtain isophorone diamine; and
   (3) subjecting the isophorone diamine to a phosgenation reaction to obtain isophorone diisocyanate,
   wherein the content of impurities containing a secondary amine group in the isophorone diamine that is subjected to the phosgenation reaction in step (3) is less than or equal to 0.5 wt %.

2. The method according to claim 1, wherein the ammonia gas in step (2) has a methylamine content of less than or equal to 0.5 wt %.

3. The method according to claim 1, wherein the hydrogen cyanide in step (1) has an olefins content of less than or equal to 0.3 wt %.

4. The method according to claim 3, wherein the olefins comprise one or more of ethylene, propylene, butylene, butadiene or isobutylene.

5. The method according to claim 1, wherein in step (1), the material molar ratio of hydrogen cyanide, isophorone and catalyst is 1:1-3:0.005-0.03.

6. The method according to claim 1, wherein the catalyst in step (1) is an oxide, a hydroxide, a cyanide, an alkyl alcoholate or a carbonate of an alkali metal or alkaline earth metal, a tertiary amine, a quaternary phosphine base or a quaternary ammonium base.

7. The method according to claim 1, wherein in step (2), the catalyst is a catalyst with an active component of cobalt or nickel.

8. The method according to claim 1, wherein the phosgenation reaction in step (3) is any one of gas phase phosgenation reaction, a cold-hot phosgenation reaction, or a salification phosgenation reaction.

9. The method according to claim 1, wherein the phosgenation reaction in step (3) is a reaction of isophorone diamine with at least one member selected from the group consisting of phosgene, diphosgene, triphosgene, fluorophosgene and bromophosgene.

10. The method according to claim 1, wherein the hydrogen cyanide in step (1) has an olefins content of less than or equal to 0.1 wt %.

11. The method according to claim 2, wherein the hydrogen cyanide in step (1) has an olefins content of less than or equal to 0.3 wt %.

12. The method according to claim 2, wherein the hydrogen cyanide in step (1) has an olefins content of less than or equal to 0.1 wt %.

13. The method according to claim 2, wherein the phosgenation reaction in step (3) is any one of gas phase phosgenation reaction, a cold-hot phosgenation reaction, or a salification phosgenation reaction.

14. The method according to claim 3, wherein the phosgenation reaction in step (3) is any one of gas phase phosgenation reaction, a cold-hot phosgenation reaction, or a salification phosgenation reaction.

15. The method according to claim 4, wherein the phosgenation reaction in step (3) is any one of gas phase phosgenation reaction, a cold-hot phosgenation reaction, or a salification phosgenation reaction.

16. The method according to claim 5, wherein the phosgenation reaction in step (3) is any one of gas phase phosgenation reaction, a cold-hot phosgenation reaction, or a salification phosgenation reaction.

17. The method according to claim 6, wherein the phosgenation reaction in step (3) is any one of gas phase phosgenation reaction, a cold-hot phosgenation reaction, or a salification phosgenation reaction.

18. The method according to claim 7, wherein the phosgenation reaction in step (3) is any one of gas phase phosgenation reaction, a cold-hot phosgenation reaction, or a salification phosgenation reaction.

19. The method according to claim 1, wherein the phosgenation reaction in step (3) a salification phosgenation reaction.

20. The method according to claim 2, wherein the phosgenation reaction in step (3) is a gas phase phosgenation reaction.

\* \* \* \* \*